United States Patent [19]

Kanesaka et al.

[11] Patent Number: 5,496,344
[45] Date of Patent: Mar. 5, 1996

[54] DILATOR FOR A BALLON CATHETER

[76] Inventors: Nozomu Kanesaka, 36 Cathy Rd.; George A. Tashji, 24 Cathy Rd., both of Hillsdale, N.J. 07642

[21] Appl. No.: 237,126

[22] Filed: May 3, 1994

[51] Int. Cl.$^6$ .......................... A61M 29/00; A61M 5/00
[52] U.S. Cl. ............................. 606/191; 604/264
[58] Field of Search .................. 606/191, 7, 13–14; 604/264, 266–267

[56] References Cited

U.S. PATENT DOCUMENTS

| | | | |
|---|---|---|---|
| 1,268,576 | 6/1918 | Jensen | 606/191 |
| 1,899,492 | 2/1933 | Beebe | 606/191 |
| 3,945,375 | 3/1976 | Banko | 606/224 |
| 4,862,891 | 9/1989 | Smith | 606/191 |
| 5,303,714 | 4/1994 | Abele et al. | 128/772 |
| 5,330,499 | 7/1994 | Kanesaka | 606/194 |
| 5,342,384 | 8/1994 | Sugarbaker | 606/191 |

Primary Examiner—Stephen C. Pellegrino
Assistant Examiner—Nancy Mulcare
Attorney, Agent, or Firm—Kanesaka & Takeuchi

[57] ABSTRACT

A dilator of the invention is used for enlarging a constricted portion of a blood vessel. The dilator is formed of a flexible guide wire to be entered into the blood vessel, a head having a tapered front portion and a through hole extending through the head, and a shaft fixed to the rear portion of the head for manipulation of the head. After the head is introduced into the blood vessel by the guide wire extending through the through hole of the head, when the head is pushed into the constricted portion by pushing the shaft, the tapered front portion enlarges the constricted portion. Thus, in case the constricted portion is too small for a balloon catheter, the constricted portion can be enlarged to a size sufficient for the balloon catheter.

9 Claims, 2 Drawing Sheets

DILATOR FOR A BALLON CATHETER

BACKGROUND OF THE INVENTION AND RELATED ART STATEMENT

The present invention relates to a dilator for a balloon catheter, more particular to a dilator for enlarging a constricted portion of a blood vessel for the balloon catheter.

A balloon dilation catheter is introduced into a body of a patient to enlarge a constricted portion of a blood vessel and other body cavities. In a conventional procedure, firstly, a guide wire is introduced into a blood vessel and manipulated to pass the constricted portion. Then, the balloon dilation catheter is inserted into the blood vessel along the guide wire. The balloon catheter is pushed into and positioned in the constricted portion, and the balloon is inflated to enlarge the constricted portion of the blood vessel.

The guide wire is a very small flexible wire with a coiled tip to protect a wall of the blood vessel. The guide wire is small enough to pass the constricted portion of the blood vessel, but in many occasions, the constricted portion is too small for the balloon catheter to pass. In this case, the operation by the balloon catheter is quitted and an alternative treatment is performed for the patient, because the constricted portion of the blood vessel can not be enlarged by the balloon.

Many attempts have been made to make a balloon catheter with a small profile at the distal or front end of the catheter. Currently, the smallest profile of the balloon catheter available on the market is still about twice the diameter of the guide wire, i.e. 0.28 inches.

There is an inherent limitation to make the balloon profile smaller since the balloon catheter must have a folded balloon and inflation/deflation tube at the balloon section, and a shaft. Also, the balloon is folded at the time of the insertion, but the folded balloon tends to loosen during the manipulation of the balloon catheter before reaching the constricted portion. This will add the difficulties to enter the balloon catheter into the constricted portion.

Accordingly, an object of the invention is to provide a dilator for a balloon catheter in order to enlarge a constricted portion of a blood vessel to allow the dilator to enter into the constricted portion prior to the insertion of the balloon catheter.

Another object of the invention is to provide a dilator as stated above, which can be exchanged with the balloon catheter easily without a trouble.

A further object of the invention is to provide a dilator as stated above, which can be made at a low cost.

Further objects and advantages of the invention will be apparent from the following description of the invention.

SUMMARY OF THE INVENTION

In accordance with the invention, a dilator is used for enlarging a constricted portion of a blood vessel. The dilator is formed of a flexible guide wire to be entered into the blood vessel, a head having a tapered front portion and a through hole extending through the head, and a shaft fixed to a rear portion of the head. The shaft is used for manipulating the head.

When the dilator is used, at first, the guide wire is introduced into the blood vessel. Then, the head is entered into the blood vessel along the guide wire passing through the through hole of the head. When the head is pushed into the constricted portion by pushing the shaft, the tapered front portion enlarges the constricted portion.

The guide wire used in the dilator may be used for guiding a balloon catheter. The tapered front portion has a front end having a smallest diameter and a rear end having a largest diameter to allow the balloon catheter to enter after the constricted portion is enlarged.

The tapered front portion may have a round profile having a spiral groove so that the head enters into the constricted portion while rotating around the guide wire. On the other hand, the tapered front portion may be formed of at least three linear faces converging at the front end. Sharp edges or blades may be formed at portions that the linear faces intersect. As a result, when the head is pushed into the constricted portion, the edges weaken the constricted portion to thereby help opening of the blood vessel when the constricted portion is enlarged by the balloon catheter.

DETAILED DESCRIPTION OF PREFERRED EMBODIMENTS

Figure 1:
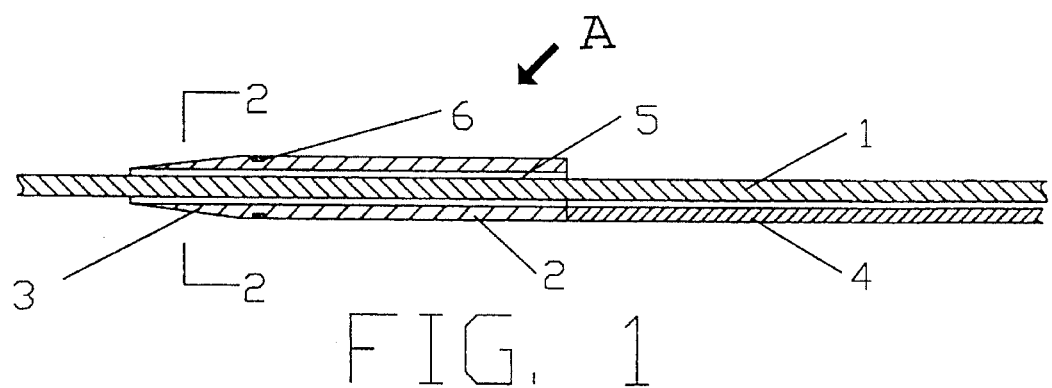
FIG. 1 is a section view of a first embodiment of a dilator of the invention.
Figures 2, 3:
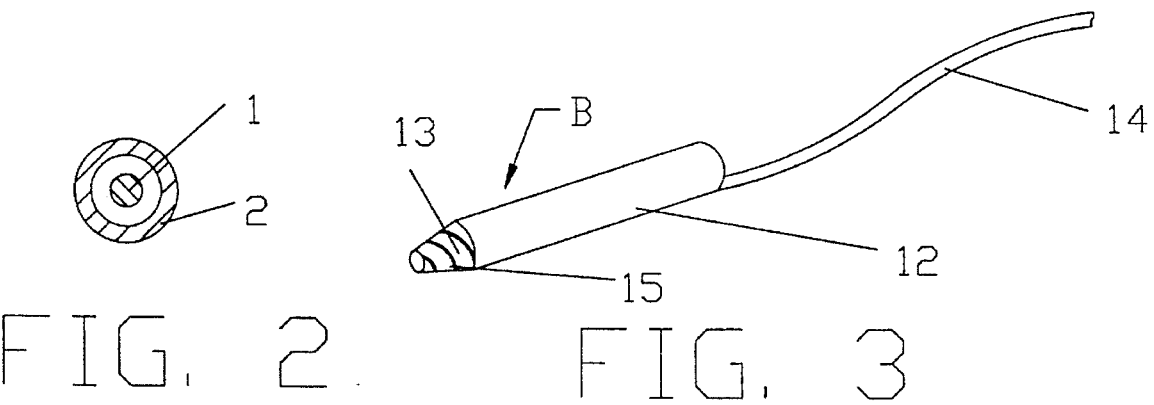
FIG. 2 is a section view taken along a line 2—2 in FIG. 1.
FIG. 3 is a perspective view of a second embodiment of a dilator of the invention.

Referring to FIGS. 1 and 2, a first embodiment A of a dilator of the invention is shown. The dilator A is formed of a guide wire 1, a head 2 having a tapered front portion 3, and a shaft 4 extending rearwardly from the rear end of the head. The head 2 includes a through hole 5, through which the guide wire 1 extends.

The head 2 and the tapered front portion 3 are round. The front end of the tapered front portion 3 has the smallest diameter, and the rear end of the tapered front portion 3 has the large diameter so that a balloon catheter can enter when a constricted portion of a blood vessel is enlarged by the dilator A. A marker band 6 is formed around the head 2, so that when a X-ray film is taken, the position of the head 2 can be identified in the film.

The head 2 has a length shorter than a distance of the blood vessel between the constricted portion and a portion that the guide wire is inserted so that the head can be easily removed from the guide wire. Generally, the length of the head may be slightly greater than a distance of the constricted portion.

The shaft 4 is simply fixed to the rear end of the head 2 to extend parallel to the guide wire 1. However, the shaft 4 may completely or partly surround the guide wire 1, while it is required that the guide wire 1 can be separated from the shaft 4 through the side thereof.

In the typical angioplasty treatment, a guide catheter (not shown) having a diameter of several millimeters and a length of about one meter is introduced from a patient's right groin through the artery to the aorta. The guide wire 1 slightly longer than the guide catheter is introduced into the blood vessel through the guide catheter and is advanced beyond the guide catheter. The guide wire 1 is further advanced to pass through a constricted portion of a blood vessel which is to be enlarged by a balloon of a balloon catheter (not shown).

The head 2 is engaged with the guide wire 1 so that the guide wire 1 passes the through hole 5. The shaft 4 is pushed to advance the head 2. After the/head 2 reaches the constricted portion, the shaft is further advanced to enlarge the constricted portion. Since the tapered portion 3 is gradually tapered to have a large diameter, the constricted portion is enlarged to the proper size.

Once the head 2 is fully inserted into the constricted portion, the dilator A or the head 2 is pulled back and the dilator A is removed from the guide wire 1 while the guide wire 1 is held in the same position. Then, the balloon catheter is engaged with the guide wire 1 and is advanced along the guide wire 1 to the constricted portion of the blood vessel. Normal procedure for the balloon catheter is then made.

FIG. 3 is a second embodiment B of the dilator of the invention. The dilator B includes a head 12, a tapered portion 13 and a shaft 14, as in the dilator A. However, the tapered portion 13 has a spiral groove 15 on the outer surface of the tapered portion 13. A plurality of spiral grooves 15 may be concentrically formed.

When the dilator B is used, the tapered portion 13 with the spiral groove 15 contacts the constricted portion of the blood vessel. Since the spiral groove 15 is formed, when the head 12 is turned around the guide wire, the head 12 can easily engage and advance through the constricted portion.

Figure 4:
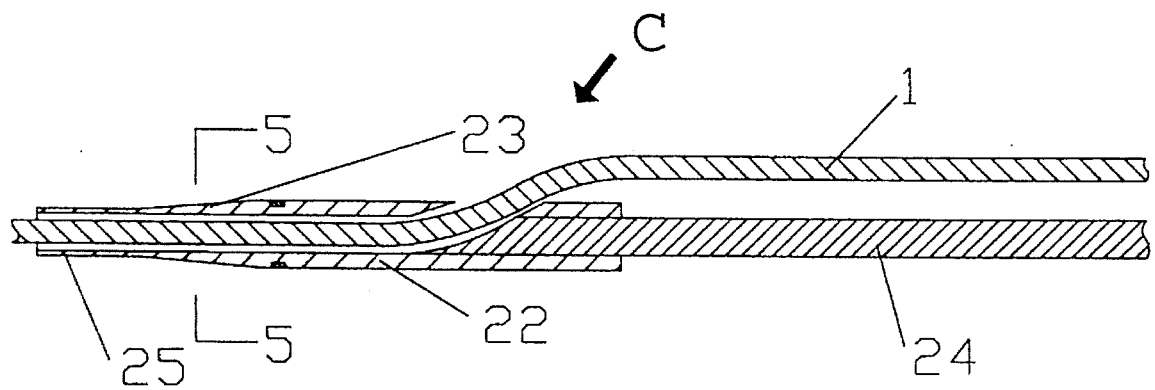
FIG. 4 is a section view of a third embodiment of a dilator of the invention.
Figure 5:
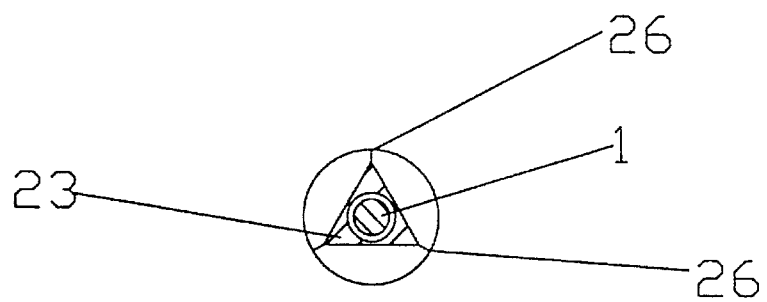
FIG. 5 is a section view taken along a line 5—5 in FIG. 4.

FIGS. 4 and 5 are third embodiment C of the dilator of the invention. The dilator C includes a head 22, a tapered portion 23 and a shaft 24, as in the dilator A. However, the tapered portion 23 has a triangular shape in section (FIG. 5) with an extension 25, while a main portion of the head 22 has a cylindrical form. The extension 25 operates to stabilize the dilator C when the dilator C is pushed or moved back and forth to the constricted portion.

In the dilator C, the tapered portion 23 has three edges 26 formed by straight side faces. When the dilator C is strongly pushed, the constricted portion of the blood vessel is urged by the edges 26 to weaken the constricted portion. Thus, when the constricted portion is later enlarged by the balloon, the constricted portion can be easily enlarged.

In the invention, in case a balloon catheter can not be inserted into a constricted portion of a blood vessel, the constricted portion can be enlarged to allow the balloon catheter to be positioned properly. Thus, even if the constricted portion is small, the balloon catheter can be positioned, and the constricted portion can be enlarged properly by the balloon catheter.

While the invention has been explained with reference to the specific embodiments of the invention, the explanation is illustrative and the invention is limited only by the appended claims.

What is claimed is:

1. A dilator adapted to be introduced into a blood vessel over a guide wire for enlarging a constricted portion of the blood vessel to introduce a balloon catheter, comprising:

a head formed of a solid material and having a tapered front portion, a rear portion integrally connected to the front portion and a through hole extending throughout an entire length of the head, said tapered front portion having distal and proximal ends and a circular cross section, said distal end of the front portion having an outer diameter less than that at said proximal end of the front portion so that the circular cross section gradually increases from the distal end to the proximal end, said guide wire being adapted to extend through the through hole in the head so that when the dilator is exchanged, the guide wire can be easily engaged with and disengaged from the head, and a shaft fixed to a part of the rear portion of the head and extending in a direction away from the tapered front portion, said shaft being actuated to enter the head into the blood vessel through the guide wire extending through the through hole of the head and being operated to move and push the head into the constricted portion, said tapered front portion enlarging the constricted portion to thereby establish a path for introducing the balloon catheter into the constricted portion after withdrawing the dilator.

2. A dilator according to claim 1, wherein said tapered front portion has a conical outer surface having a spiral groove thereon, said spiral groove defining spiral edges at both rims of the spiral groove on the conical outer surface so that when the tapered front portion is rotated around the guide wire, said edge engages the constricted portion and advance through the constricted portion.

3. A dilator according to claim 1, wherein said head has a length shorter than a distance of the blood vessel between the constricted portion and a portion that the guide wire is inserted so that the head can be easily removed from the guide wire.

4. A dilator according to claim 3, wherein said length of the head is greater than a distance of the constricted portion.

5. A dilator according to claim 1, wherein said rear portion has a uniform diameter same as the diameter of the proximal end of the front portion.

6. A dilator according to claim 1, wherein a length of the rear portion of the head and a length of the front portion is substantially in a ratio of 2:5.

7. A dilator adapted to be introduced into a blood vessel over a guide wire for enlarging a constricted portion of the blood vessel to introduce a balloon catheter, comprising:

a head having a tapered front portion, a rear portion and a through hole extending through the head, said tapered front portion including a front end and a rear end having a length perpendicularly to a longitudinal direction of the head greater than a length at the front end and being formed of at least three linear faces converging toward the front end and edges formed by two of the linear faces intersecting together so that the edges weaken the constricted portion when the head is actuated, and a shaft fixed to the rear portion of the head, said shaft being actuated to manipulate the head when the head is pushed into the constricted portion to enlarge the constricted portion by the at least three linear faces.

8. A dilator according to claim 7, wherein the rear portion of the head has a hole on a side wall of the rear portion, said hole communicating the through hole for introducing the guide wire, the shaft being attached to the rear portion.

9. A combination of a dilator adapted to enlarge a constricted portion of a blood vessel and a guide wire for introducing the dilator into the blood vessel to introduce a balloon catheter, wherein said dilator includes;

a head formed of a solid material and having a tapered front portion, a rear portion integrally connected to the front portion and a through hole extending throughout an entire length of the head, said tapered front portion having distal and proximal ends and a circular cross section, said distal end of the front portion having an outer diameter less than that at the proximal end of the front portion so that the circular cross section gradually increases from the distal end to the proximal end, said guide wire extending through the through hole in the head so that when the dilator is exchanged, the guide wire can be easily engaged with and disengaged from the head, and a shaft fixed to a part of the rear portion of the head and extending in a direction away from the tapered front portion, said shaft being actuated to enter the head into the blood vessel through the guide wire extending through the through hole of the head and being operated to move and push the head into the constricted portion, said tapered front portion enlarging the constricted portion to thereby establish a path for introducing the balloon catheter into the constricted portion after withdrawing the dilator.

* * * * *